United States Patent
Jones et al.

(10) Patent No.: US 8,931,481 B2
(45) Date of Patent: Jan. 13, 2015

(54) FLOW GENERATOR CHASSIS ASSEMBLY WITH SUSPENSION SEAL

(75) Inventors: Richard Llewelyn Jones, Hornsby Heights (AU); Saad Nasr, Oatley (AU); Joern Lange, Neutral Bay (AU); Ernie Wei-Chih Tsai, Mortdale (AU); Barton John Kenyon, Ashfield (AU); Geoffrey Crumblin, Baulkham Hills (AU)

(73) Assignee: RedMed Limited, Bella Vista (AU)

( * ) Notice: Subject to any disclaimer, the term of this patent is extended or adjusted under 35 U.S.C. 154(b) by 854 days.

(21) Appl. No.: 12/794,206

(22) Filed: Jun. 4, 2010

(65) Prior Publication Data

US 2010/0307498 A1 Dec. 9, 2010

Related U.S. Application Data

(60) Provisional application No. 61/184,124, filed on Jun. 4, 2009.

(51) Int. Cl.
*A61M 16/00* (2006.01)
*F04D 29/60* (2006.01)
(Continued)

(52) U.S. Cl.
CPC .......... *F04D 29/601* (2013.01); *F04D 29/4226* (2013.01); *A61M 2205/3368* (2013.01); *A61M 2016/0027* (2013.01); *A61M 16/0066* (2013.01); *A61M 2205/42* (2013.01); *A61M 2016/003* (2013.01)
USPC .................................................. 128/204.18

(58) Field of Classification Search
USPC ............. 128/200.24, 204.14, 204.17, 204.18, 128/204.21, 205.18, 202.27, 203.12; 417/423.11, 423.14, 363; 248/638, 248/634; 415/119, 214.1
See application file for complete search history.

(56) References Cited

U.S. PATENT DOCUMENTS 4,913,951 A * 4/1990 Pitolaj .............................. 428/76
6,231,052 B1 * 5/2001 Forlander ....................... 277/616
(Continued)

FOREIGN PATENT DOCUMENTS

WO WO 2007/019625 A1 2/2007
WO WO 2007/048205 A1 5/2007
(Continued)

*Primary Examiner* — Jackie T Ho
*Assistant Examiner* — Mark Wardas
(74) *Attorney, Agent, or Firm* — Nixon & Vanderhye P.C.

(57) ABSTRACT

A seal is provided for a chassis assembly of a flow generator configured to provide a flow of breathable gas. The chassis assembly includes an upper chassis and a lower chassis. The seal includes a blower receptacle sealing portion configured to seal a blower receptacle of the chassis assembly configured to receive a blower configured to generate the flow of breathable gas; a flow sensor sealing portion configured to seal a flow sensor provided in the chassis assembly and configured to measure the flow of breathable gas; a blower mount configured to receive a portion of the blower and mount the blower to the seal; and a blower mount suspension configured to connect the blower mount to the blower receptacle sealing portion, wherein in an assembled condition the seal and the chassis assembly define a flow path from an inlet of the chassis assembly to the blower receptacle of the chassis assembly to an outlet of the chassis assembly. A flow generator for generating a flow of breathable gas includes a chassis assembly comprising a lower chassis and an upper chassis, the lower chassis and the upper chassis defining a blower receptacle; a blower provided in the blower receptacle; and the seal.

71 Claims, 19 Drawing Sheets

(51) Int. Cl.
*F04D 29/42* (2006.01)
*A62B 7/00* (2006.01)

(56) References Cited

U.S. PATENT DOCUMENTS

| | | |
|---|---|---|
| 6,315,526 B1 | 11/2001 | Jones |
| 6,837,260 B1 * | 1/2005 | Kuehn ............... 137/315.01 |
| 7,571,725 B2 | 8/2009 | Wickham et al. |
| 7,891,573 B2 * | 2/2011 | Finkam et al. ............ 236/49.3 |
| 7,909,032 B2 * | 3/2011 | Feldhahn et al. ....... 128/204.14 |
| 7,967,576 B2 * | 6/2011 | Abate et al. ................ 417/360 |
| 8,051,852 B2 * | 11/2011 | Bassin ...................... 128/204.18 |
| 2008/0162226 A1 * | 7/2008 | Maresca et al. ................ 705/7 |
| 2008/0304986 A1 | 12/2008 | Kenyon et al. |
| 2009/0162226 A1 * | 6/2009 | Campbell .............. 417/423.14 |
| 2010/0065051 A1 * | 3/2010 | Potharaju et al. ....... 128/203.26 |
| 2010/0320755 A1 * | 12/2010 | Williams et al. ............ 285/355 |

FOREIGN PATENT DOCUMENTS

| | | |
|---|---|---|
| WO | WO 2007/048206 A1 | 5/2007 |
| WO | WO 2007/134405 A1 | 11/2007 |

* cited by examiner

FLOW GENERATOR CHASSIS ASSEMBLY WITH SUSPENSION SEAL

CROSS REFERENCE TO RELATED APPLICATIONS

This application claims the benefit of U.S. application Ser. No. 61/184,124, filed Jun. 4, 2009, the entire contents of which are incorporated herein by reference.

FIELD OF THE INVENTION

The present technology relates to a flow generator for generating a flow of breathable gas to be delivered to a patient. In an embodiment, the flow generator may be used in a positive airway pressure (PAP) device used for the delivery of respiratory therapy to a patient. Examples of such therapies are Continuous Positive Airway Pressure (CPAP) treatment, Non-Invasive Positive Pressure Ventilation (NIPPV), Variable Positive Airway Pressure (VPAP), and Bi-Level Positive Airway Pressure. The therapy is used for treatment of various respiratory conditions including Sleep Disordered Breathing (SDB) and more particularly Obstructive Sleep Apnea (OSA). The present technology also relates to a seal for the flow generator. The present technology further relates to methods of assembling a flow generator.

BACKGROUND

Flow generators are used to generate a flow of breathable gas for treatment of various respiratory conditions. The flow generator may be configured to be connected to a patient interface, for example a mask, to deliver the flow of breathable gas to the patient's airways. The flow generator may also be configured to be connected to a humidifier configured to store a supply of water for humidifying the flow of breathable gas prior to delivery to the patient.

A blower is provided in the flow generator to generate the flow of breathable gas. A blower may comprise a motor comprising a rotating part including, for example, a shaft having an impeller(s) mounted thereon, and a non-rotating part. The operation of the motor may generate noise and vibration. As the therapy may be delivered to the patient during sleep, the generation of noise and vibration may reduce the effectiveness of the therapy.

The flow generator may also include electronics configured to control the operation of the motor of the blower to vary the pressure of the flow of breathable gas that is generated by the blower. The electronics may be damaged by the flow of breathable gas generated by the blower, for example by debris drawn into the flow generator.

A flow sensor may be provided to measure the volume of the flow of breathable gas generated by the blower. Gaps in the flow generator chassis assembly may allow portions of the flow of breathable gas to bypass the flow sensor, thus providing an inaccurate measure of the flow.

BRIEF SUMMARY

According to one aspect, a flow generator chassis assembly is provided with a seal that is configured to mount the blower.

According to another aspect, the seal is configured to align the motor of the blower.

According to still another aspect, the seal is configured as a suspension for the blower.

According to a further aspect, the seal is configured to seal between high and low pressure sides of the flow generator chassis assembly.

According to yet another aspect, the seal is configured to seal an inlet air flow path and/or an outlet air flow path of the flow generator chassis assembly.

According to another aspect, the seal is configured to seal a portion of the flow generator chassis assembly from which a wire of the blower motor extends out of the chassis assembly.

According to a further aspect, the seal is configured to seal between acoustic chambers of the flow generator chassis assembly.

According to still another aspect, the seal is configured to seal an air flow path through the flow generator chassis assembly from electronics contained in the flow generator chassis assembly.

According to yet another aspect, the seal may be configured to include a flow sensor tube seal and a manifold connection to the flow sensor.

According to one sample embodiment of the technology, a seal is provided for a chassis assembly of a flow generator configured to provide a flow of breathable gas. The chassis assembly includes an upper chassis and a lower chassis. The seal comprises a blower receptacle sealing portion configured to seal a blower receptacle of the chassis assembly configured to receive a blower configured to generate the flow of breathable gas; a flow sensor sealing portion configured to seal a flow sensor provided in the chassis assembly and configured to measure the flow of breathable gas; a blower mount configured to receive a portion of the blower and mount the blower to the seal; and a blower mount suspension configured to connect the blower mount to the blower receptacle sealing portion, wherein in an assembled condition the seal and the chassis assembly define a flow path from an inlet of the chassis assembly to the blower receptacle of the chassis assembly to an outlet of the chassis assembly.

According to another sample embodiment, a flow generator for generating a flow of breathable gas comprises a chassis assembly comprising a lower chassis and an upper chassis, the lower chassis and the upper chassis defining a blower receptacle; a blower provided in the blower receptacle; and a seal according to at least the preceding paragraph.

According to still another sample embodiment, a method of assembling a flow generator, for example as described above, comprises mounting the blower to the blower mount of the seal; positioning the seal on the lower chassis; routing the wire of the blower through the grommet of the seal; and fastening the upper chassis and the lower chassis together.

According to yet another sample embodiment, a method of assembling a flow generator, for example as described above, comprises mounting the blower to the blower mount of the seal; aligning the seal on the upper chassis; positioning the lower chassis on the seal; and fastening the upper chassis and the lower chassis together.

According to a further sample embodiment, a flow generator for generating a pressurized flow of breathable gas comprises a chassis comprising a lower chassis and an upper chassis, the lower chassis and the upper chassis defining an enclosure; a blower provided in the enclosure and configured to generate a flow of breathable gas from air drawn through an inlet in the chassis and deliver the flow of breathable gas to an outlet in the chassis; and a blower mount between the lower chassis and the upper chassis that mounts the blower in the enclosure. The blower mount comprises a blower receptacle that receives a lower portion of the blower, a blower mount outlet configured to deliver the flow of breathable gas from the blower to the outlet in the chassis, and a seal in engagement with the upper chassis to provide a sealed air flow path from an inlet of a upper chassis blower receptacle to the blower mount outlet.

Other aspects, features, and advantages of the technology will become apparent from the following detailed description when taken in conjunction with the accompanying drawings, which are a part of this disclosure and which illustrate, by way of example, principles of the technology.

BRIEF DESCRIPTION OF THE DRAWINGS

The accompanying drawings facilitate an understanding of the various embodiments of this invention. In such drawings.

DETAILED DESCRIPTION OF THE ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

Chassis

Figure 1:
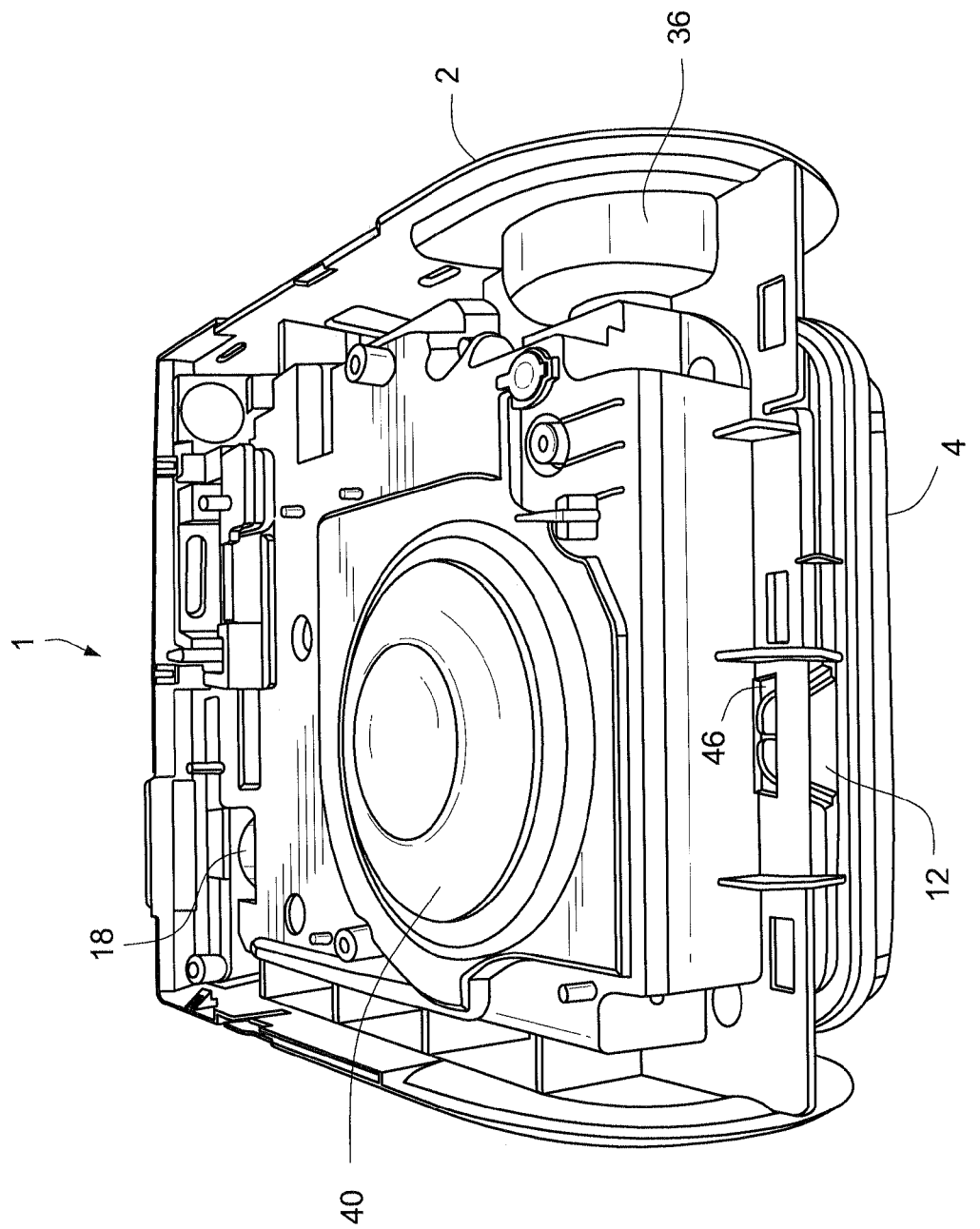
FIG. 1 is a top perspective view of a flow generator according to a sample embodiment.
Figure 2:
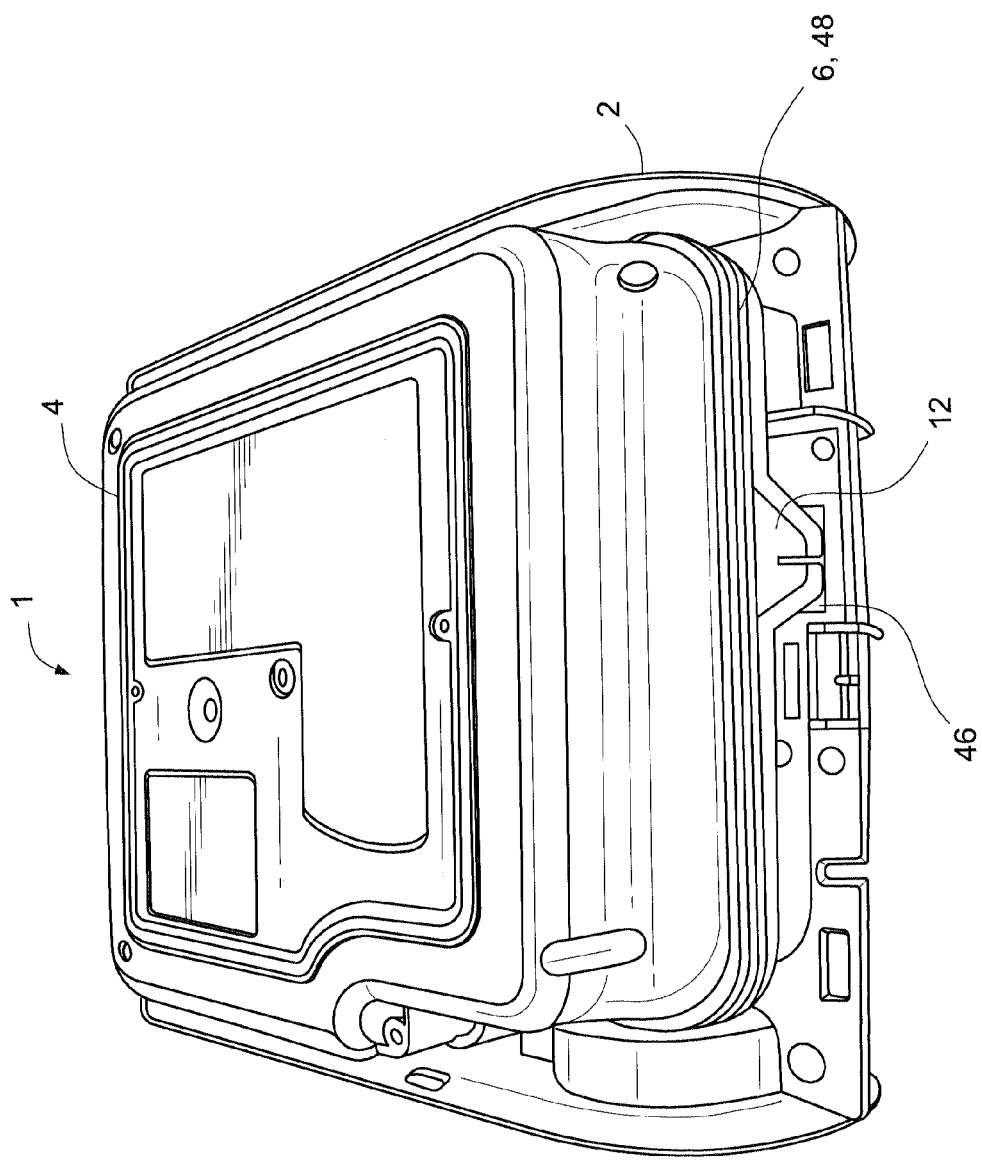
FIG. 2 is a bottom perspective of the flow generator of FIG. 1.
Figure 3:
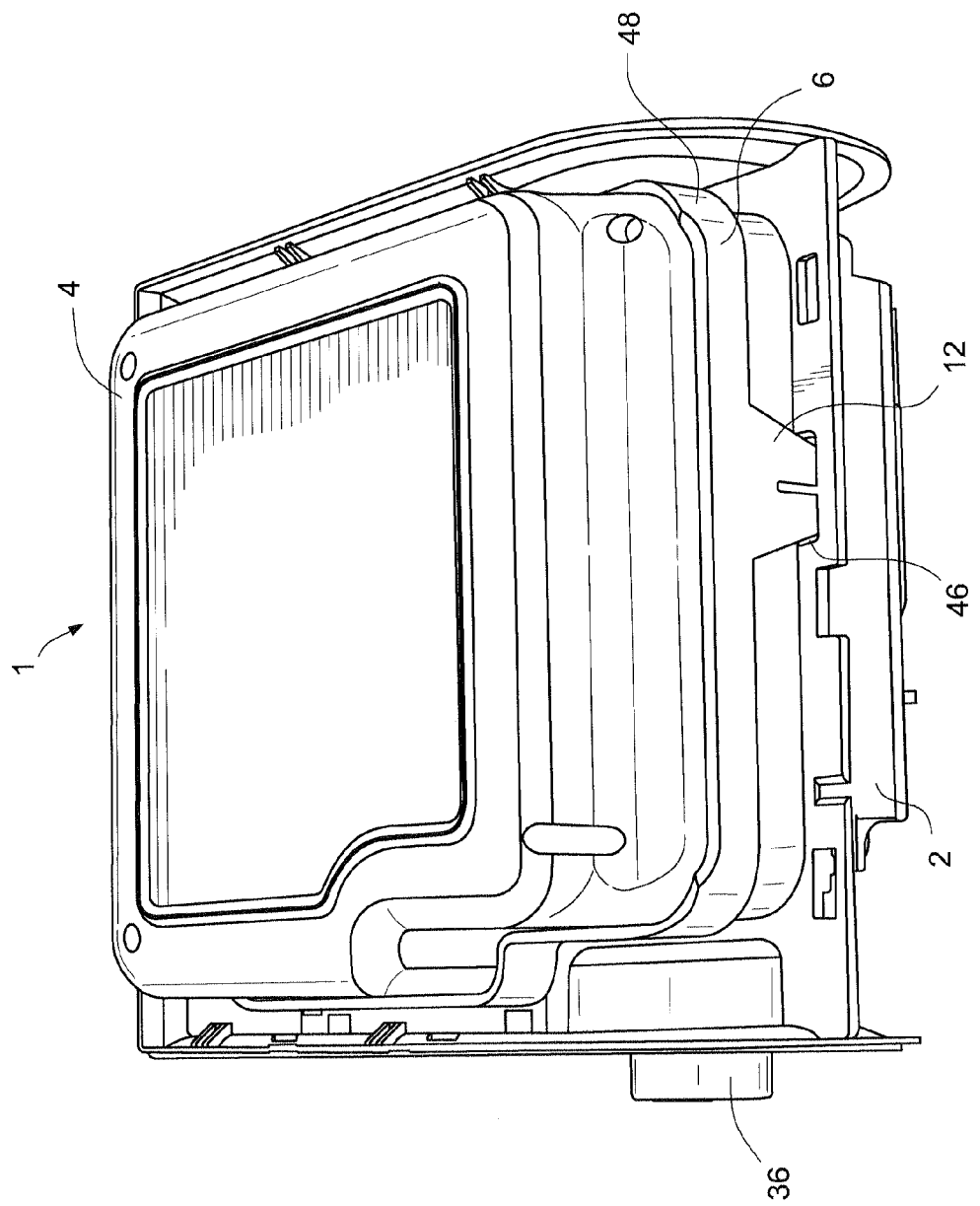
FIG. 3 is a bottom perspective of the flow generator of FIG. 1.
Figure 4:
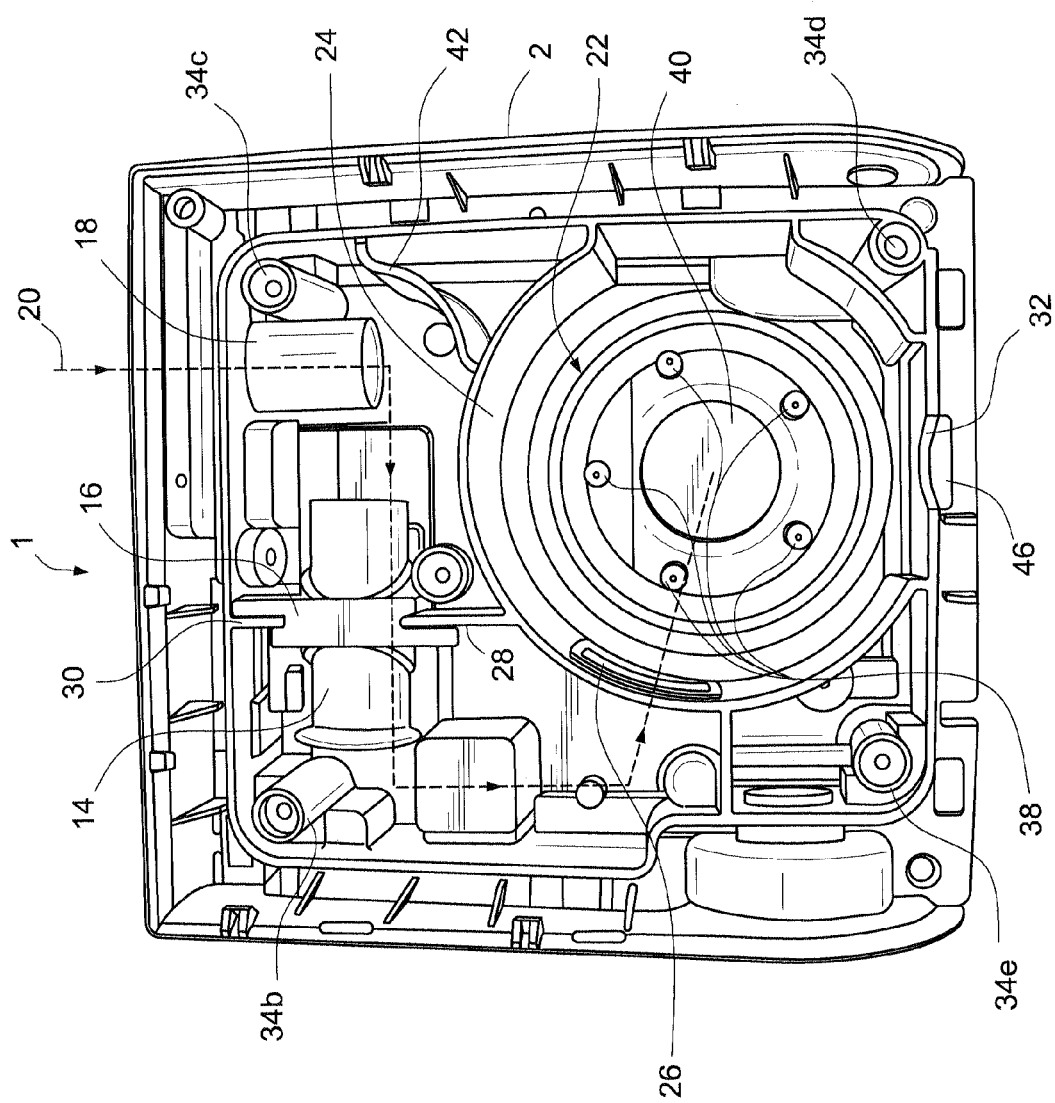
FIGS. 4-7 are perspective views of the upper chassis of the flow generator according to a sample embodiment.
Figure 19:
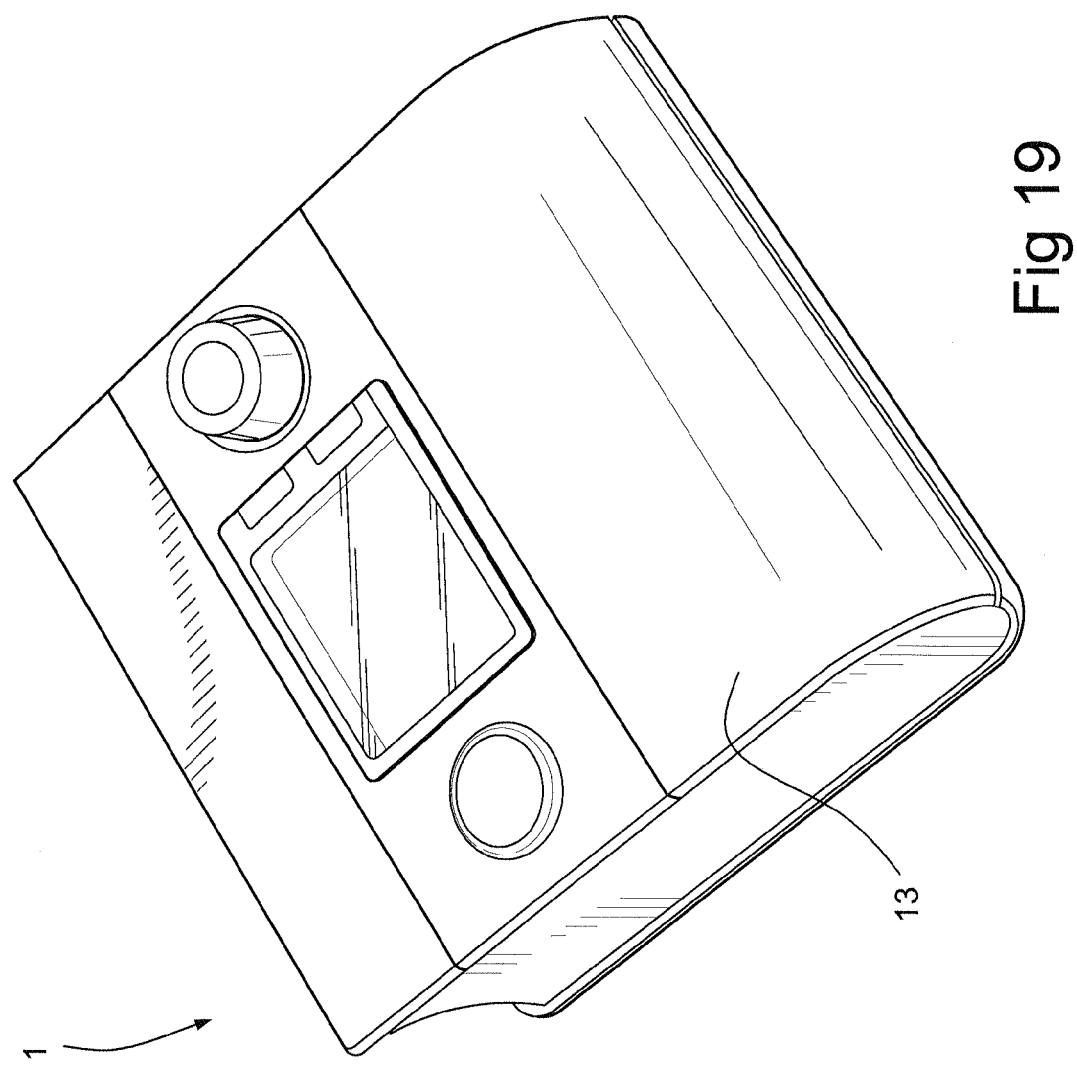
FIG. 19 is a perspective view of the flow generator including an outer casing.

Referring to FIG. 1, a chassis assembly of a flow generator 1 includes an upper chassis 2 and a lower chassis 4. The upper chassis 2 and the lower chassis 4 may be formed of, for example, plastic. The upper chassis 2 includes an air flow outlet 36 that is configured to be connected to a tube or conduit for delivery of a flow of breathable gas to a patient interface that is configured to engage the patient to deliver the flow of breathable gas. It should also be appreciated that the air flow outlet 36 is configured to be connected to the inlet of a humidifier configured to store a supply of water for humidifying the flow of breathable gas. Referring to FIG. 19, the flow generator 1 may comprise an outer casing 13 that covers and/or surrounds the chassis assembly.

The upper chassis 2 also includes an upper chassis receptacle top portion 40 that is configured to receive the top of a blower 10 (FIG. 13) described in more detail below. The blower is configured to generate the flow of breathable gas, e.g. in the range of about 2-30 cm $H_2O$, from air drawn through an air inlet 18 provided in the upper chassis 2.

A grommet 12 of a flow generator seal extends through a grommet slot 46 provided in the upper chassis 2.

Blower Mount

Referring to FIGS. 2, 3, 8 and 9, the blower mount, or flow generator seal, 6 is provided between the upper chassis 2 and the lower chassis 4. As discussed in more detail below, the flow generator seal 6 provides a sealed inlet air path for the flow generator 1. The sealed inlet air path directs the inlet air flow through an inlet filter and prevents the air flow from leaking through gaps in the case formed by the upper chassis 2 and the lower chassis 4. The inlet air flow thus does not flow over the electronics. The sealing of the air flow also reduces noise leakage through the gaps in the case. It should be appreciated, however, that the flow generator seal 6 may not include an inlet air path seal.

As shown in FIGS. 2, 3, 8, 9, 12-15 and 17, the flow generator seal 6 includes a flow generator seal skirt 48 having a T-shaped cross section that extends around the perimeter of the flow generator seal 6 and engages the upper chassis 2 and the lower chassis 4 to seal the junction between the upper chassis 2 and the lower chassis 4.

The seal 6 may be formed of a flexible material, for example silicone. The seal may also be formed so as to be elastically deformable, for example to stretch, to permit the seal to engage various portions of the flow generator chassis assembly and/or blower while in a deformed, e.g. stretched, condition. The seal may also be transparent or translucent. In other sample embodiments, the seal may also comprise a frame or support, e.g. a rigid support skeleton, that may be, for example, overmolded onto the flexible material (or the flexible material of the seal may be overmolded onto the frame or support), that provides additional locations for other components of the flow generator and/or aids in assembly of the flow generator.

Upper Chassis

Referring to FIGS. 4-7, the upper chassis 2 comprises the air inlet 18. An air inlet flow path 20 is established by the operation of a blower that is provided in an upper chassis blower receptacle 22 when the upper chassis 2, the flow generator seal 6, and the lower chassis 4 are assembled. The air inlet flow path 20 includes a flow sensor 14 that is supported in the upper chassis 2 between a pair of interior walls 28, 30. A flow sensor seal 16 is provided to prevent the inlet air flow path 20 from bypassing the flow sensor 14. It should be appreciated that the flow sensor seal 16 may be provided separately from the seal 6. It should also be appreciated that the flow sensor seal 16 may be integrally formed with the seal 6 and include the manifold connection to the flow sensor 14. It should be further appreciated that other sensors, e.g. pressure and/or thermistor, may be sealed, for example by integrally forming other sensor seals with the flow generator seal 6.

After passing through the flow sensor 14, the inlet air flow path 20 passes through a side wall air inlet 26 provided in the upper chassis blower receptacle side wall 24. The upper chassis blower receptacle 22 comprises a plurality of upper chassis bump stops 38 and a grommet notch 32 that is configured to receive the grommet 12 of the flow generator seal 6 that is configured to hold the electrical wire extending from the blower that is contained in the upper chassis blower receptacle 22. The upper chassis 2 also comprises a grommet slot 46 that the grommet 12 passes through.

A plurality of upper chassis fastener receptacles 34a-34e are provided in the upper chassis 2 and are configured to receive fasteners 88 (FIG. 18) that are configured to assemble the upper chassis 2, the flow generator seal 6 and the lower chassis 4 in to the flow generator 1.

Figure 5:
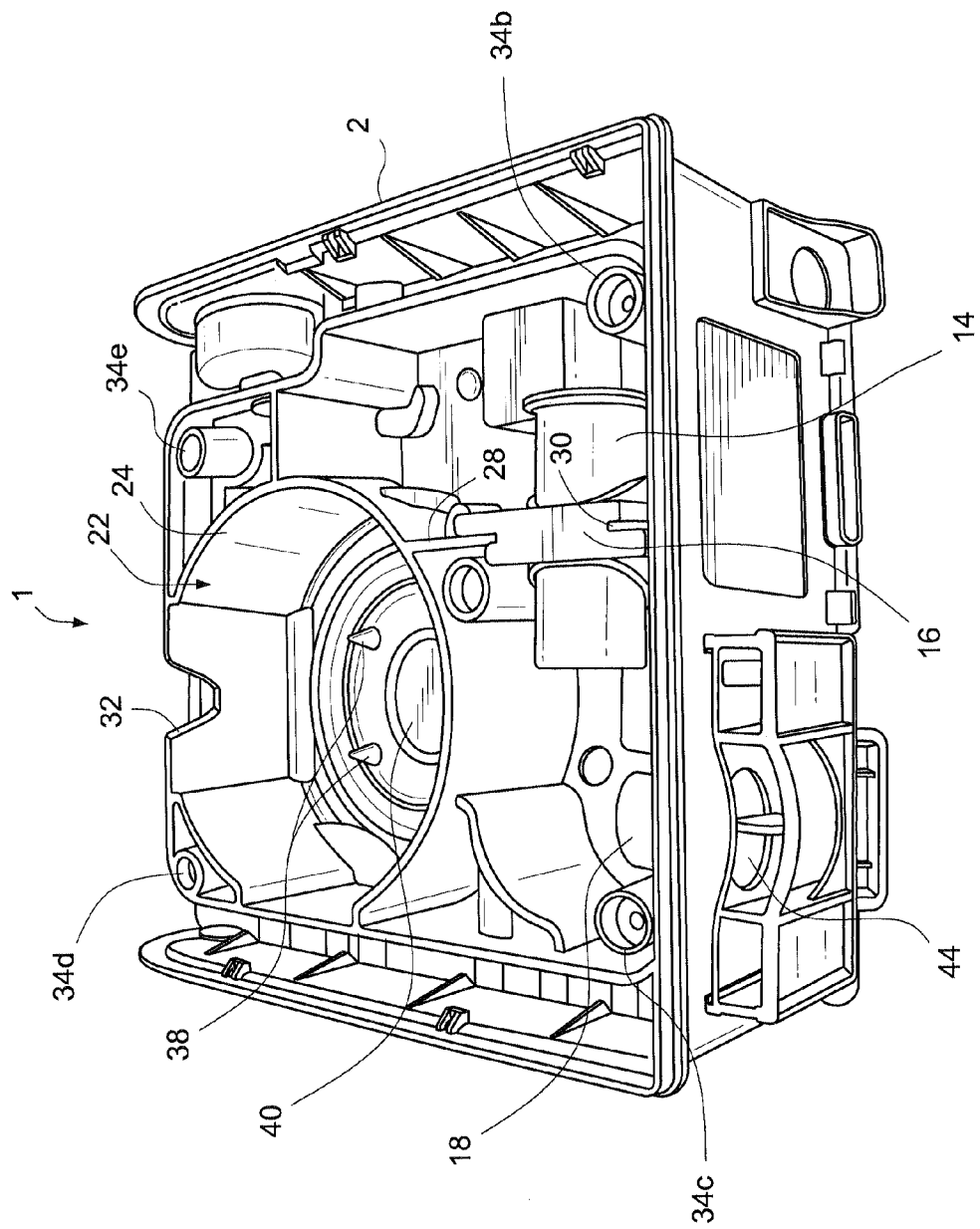
Figure 6:
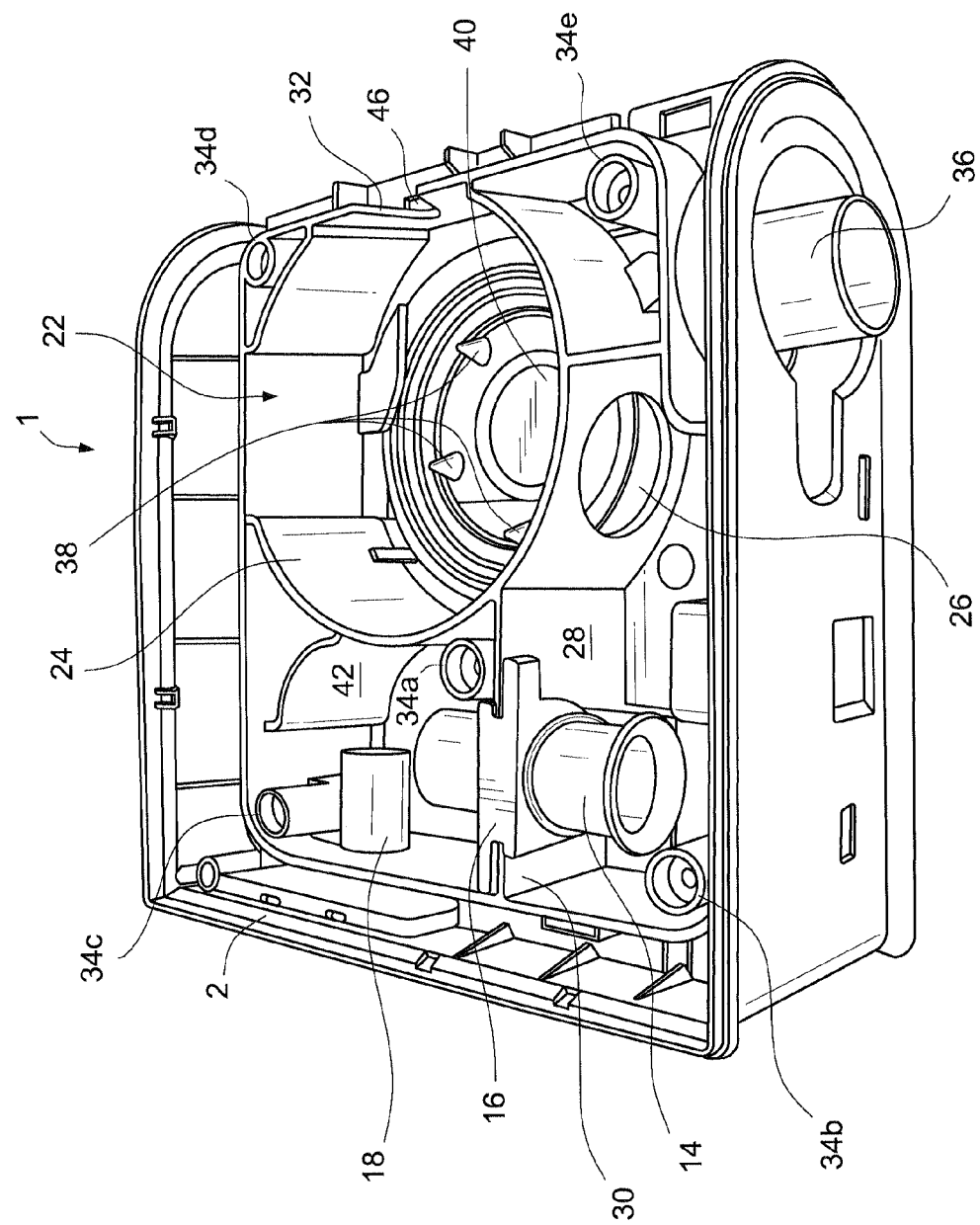
Figure 7:
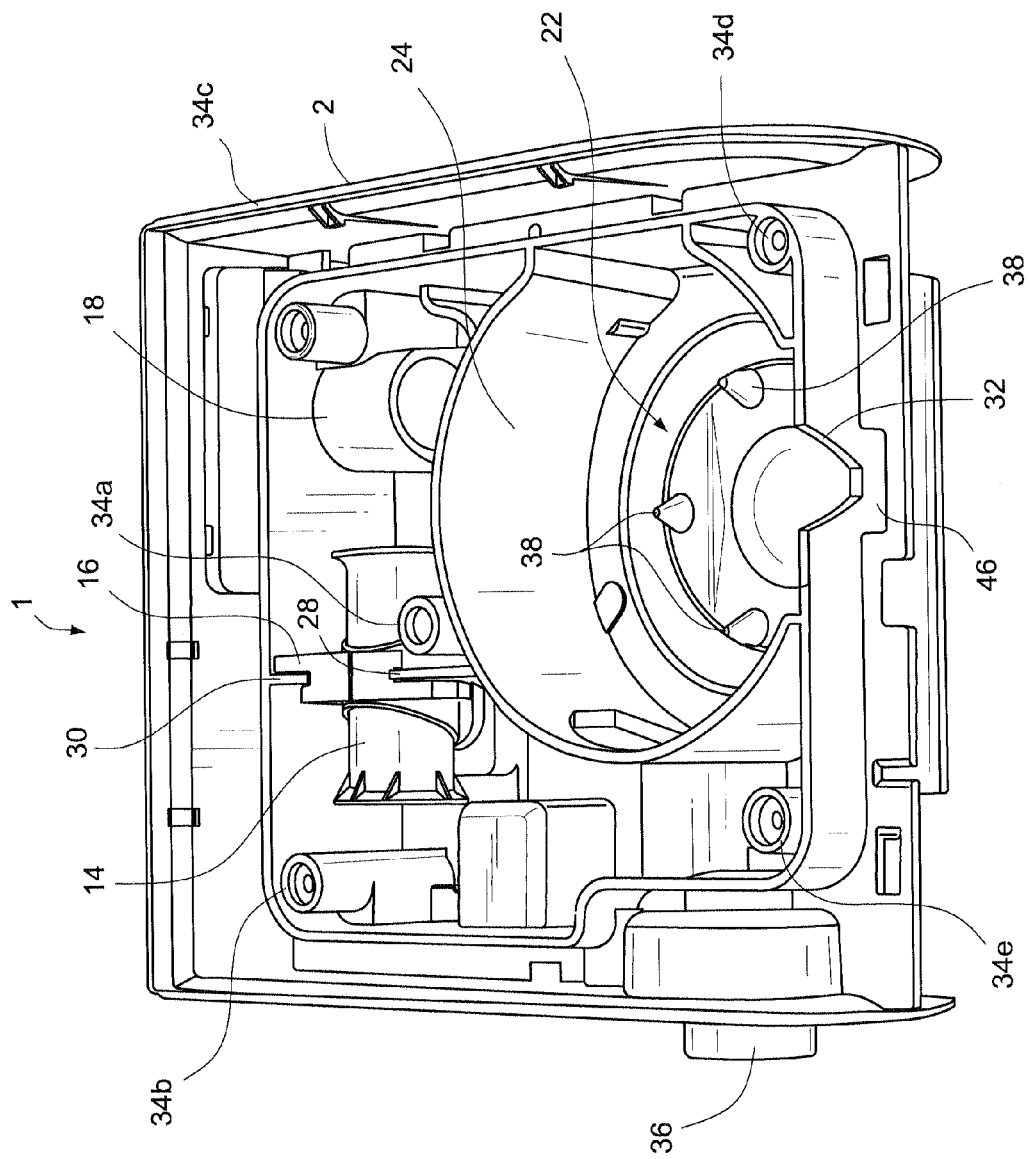

As shown in FIG. 5, the air inlet 18 of the upper chassis 2 includes an air inlet aperture 44 formed on a side wall of the upper chassis 2. It should be appreciated that an air inlet filter may be provided at the air inlet aperture 44 to filter air drawn in to the flow generator 1 by the blower.

Figure 8:
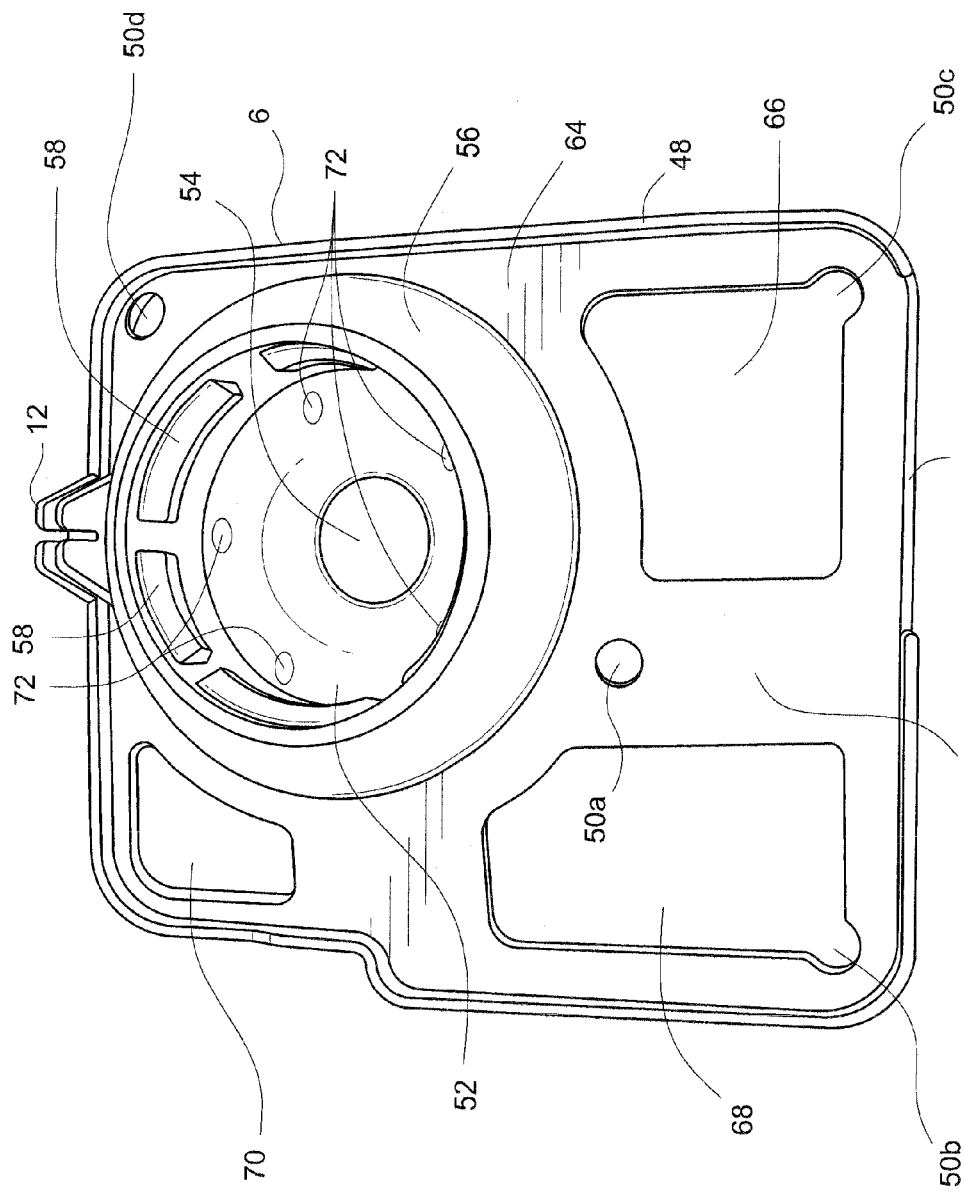
FIG. 8 is a top perspective view of a flow generator seal according to a sample embodiment.
Figure 9:
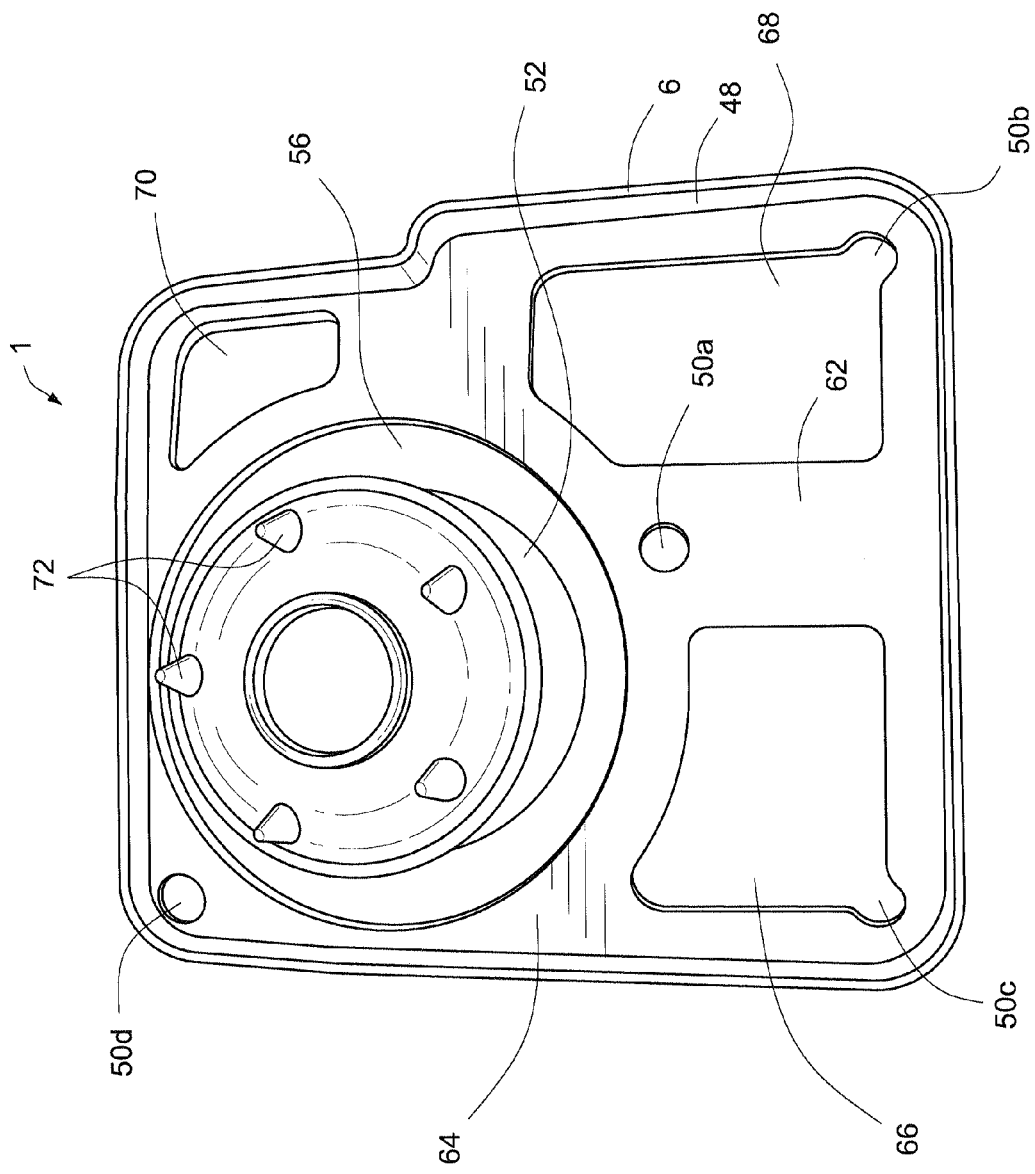
FIG. 9 is a bottom perspective view of the flow generator seal of FIG. 8.

Referring to FIGS. 8 and 9, the flow generator seal 6 comprises the T-shaped skirt 48 that extends around the perimeter of the flow generator seal 6. As shown in FIG. 8, a flow generator seal inlet portion 60 is provided on the flow generator seal 6. The T-shaped skirt 48 does not extend above the perimeter of the flow generator seal 6 in this region of the flow generator seal inlet portion 60 which is configured to be aligned with the air inlet aperture 44 and the air inlet 18 of the upper chassis 2. The skirt is L-shaped in cross section in the region of the seal inlet portion 60 and extends below the perimeter of the flow generator seal 6 and engages the perimeter of the lower chassis 4.

On the side opposite of the flow generator seal inlet portion 60, the flow generator seal 6 comprises the wire grommet 12 that is configured to hold the wire extending from the motor of the blower. A flow sensor seal portion 62 extends between the side including the inlet portion 60 and a blower receptacle and mount suspension 56 provided on the flow generator seal 6. The wire grommet 12 may be located at other positions on the seal 6, however locating the wire grommet 12 adjacent to the blower receptable and mount suspension 56 minimizes the length of the wires.

The blower receptacle and mount suspension 56 has a frusto-conical shape and supports a blower receptacle and mount 52 that is configured to receive a portion of the blower. As shown in FIG. 9, the blower receptacle and mount 52 comprises a plurality of flow generator seal bump stops 72 that are configured to prevent the blower bumping into the lower chassis 4.

The blower receptacle and mount 52 also comprises a plurality of blower receptacle and mount ribs 58 spaced around a periphery of the receptacle and mount 52 that are configured to engage the blower. The blower receptacle mount 52 also comprises a blower receptacle and mount outlet 54 through which the flow of breathable gas generated by the blower passes through to the outlet 36 of the flow generator 1.

The flow generator seal 6 includes a plurality of flow generator seal fastener openings 50a-50d that correspond to the upper chassis fastener receptacles 34a-34d. The fastener openings 50a-50d allow the fasteners to pass through to permit the upper chassis 2, the flow generator seal 6, and a lower chassis 4 to be assembled in to the flow generator 1.

A blower receptacle seal portion 64 extends circumferentially around the blower receptacle and mount suspension 56 and is configured to provide a seal around the blower received in the blower receptacle and mount 52. An air inlet seal opening 66 is provided adjacent to the blower receptacle seal portion 64 and the air inlet flow path 20 passes the air inlet seal opening in to the side wall air inlet 26 of the side wall 24 of the blower receptacle 22 of the upper chassis 2.

The air inlet seal opening 66 is provided adjacent to the blower receptacle seal portion 64 in the region of the air inlet 18 of the upper chassis 2 to permit the inlet air flow path to enter the flow generator 1 through the air inlet 18. An air flow outlet seal opening 70 is provided adjacent to the blower receptacle seal portion 64 so that the flow of breathable gas produced by the blower can pass to the outlet 36 of the flow generator 1.

Lower Chassis

Figure 10:
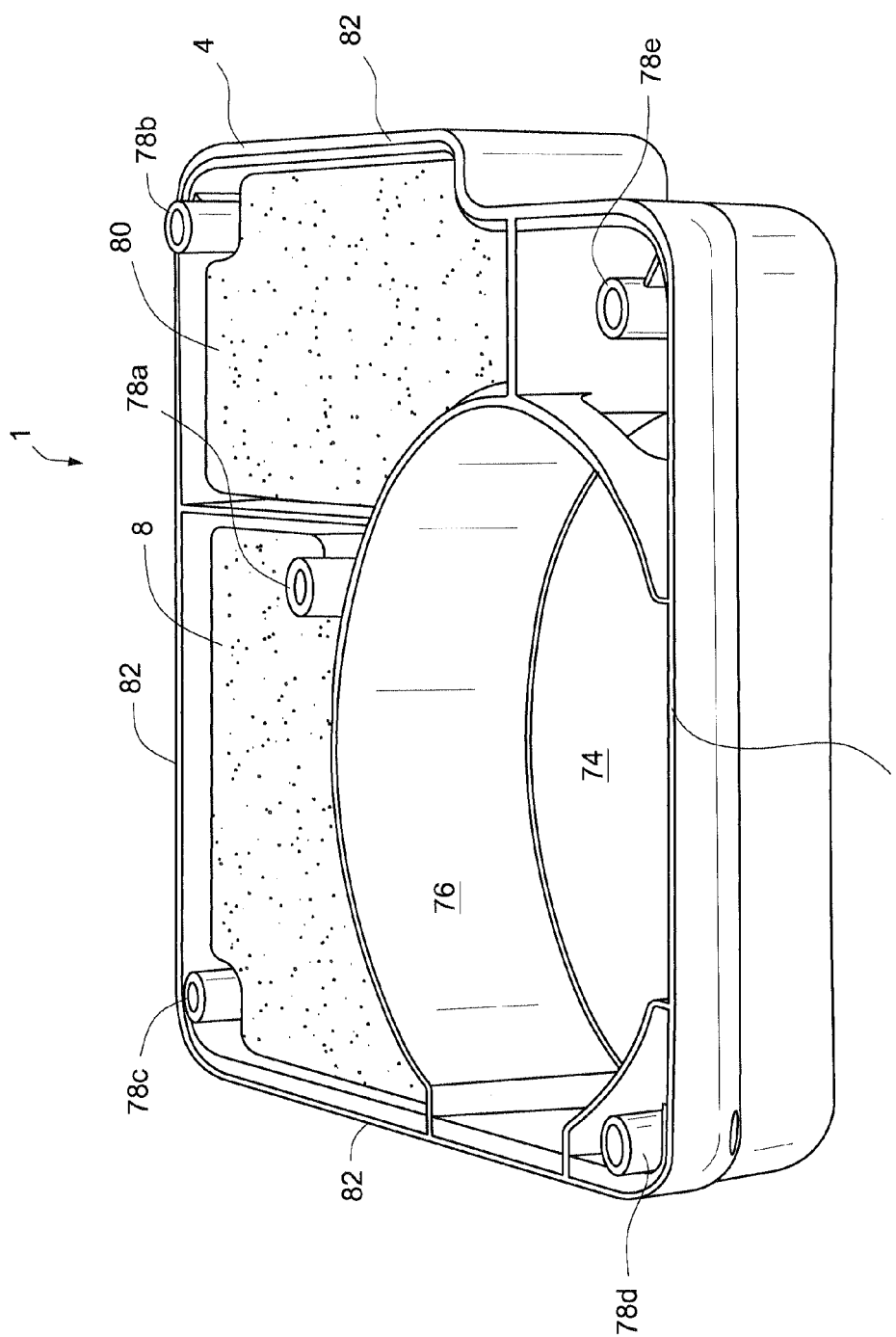
FIG. 10 is a perspective view of a lower chassis of the flow generator according to a sample embodiment.

Referring to FIG. 10, the lower chassis 4 includes a lower chassis blower receptacle 74 that comprises a lower chassis blower receptacle side wall 76 that is configured to receive a portion of the blower. A plurality of lower chassis fastener receptacles 78a-78e are provided that correspond to the upper chassis fastener receptacle openings 34a-34e and the flow generator seal fastener openings 50a-50d.

Referring still to FIG. 10, the compartment of the lower chassis 4 that corresponds to the blower inlet seal opening 68 of the flow generator seal 6 may comprise a foam 80. The compartment of the lower chassis 4 that corresponds to the air inlet seal opening 66 of the flow generator seal 6 may comprise a foam 8.

Figure 11:
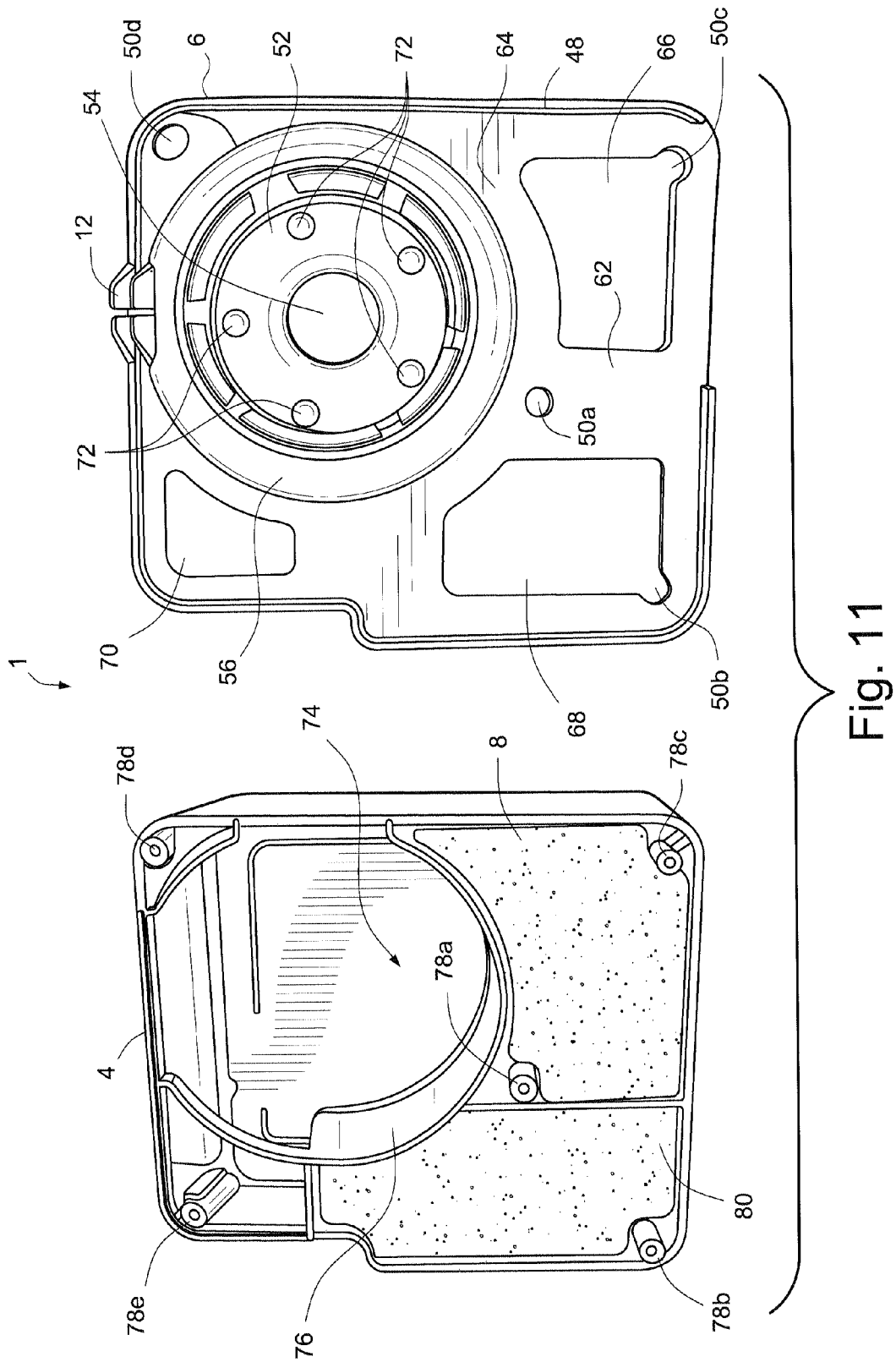
FIG. 11 is a perspective view of the lower chassis and the flow generator seal prior to assembly.
Figure 12:
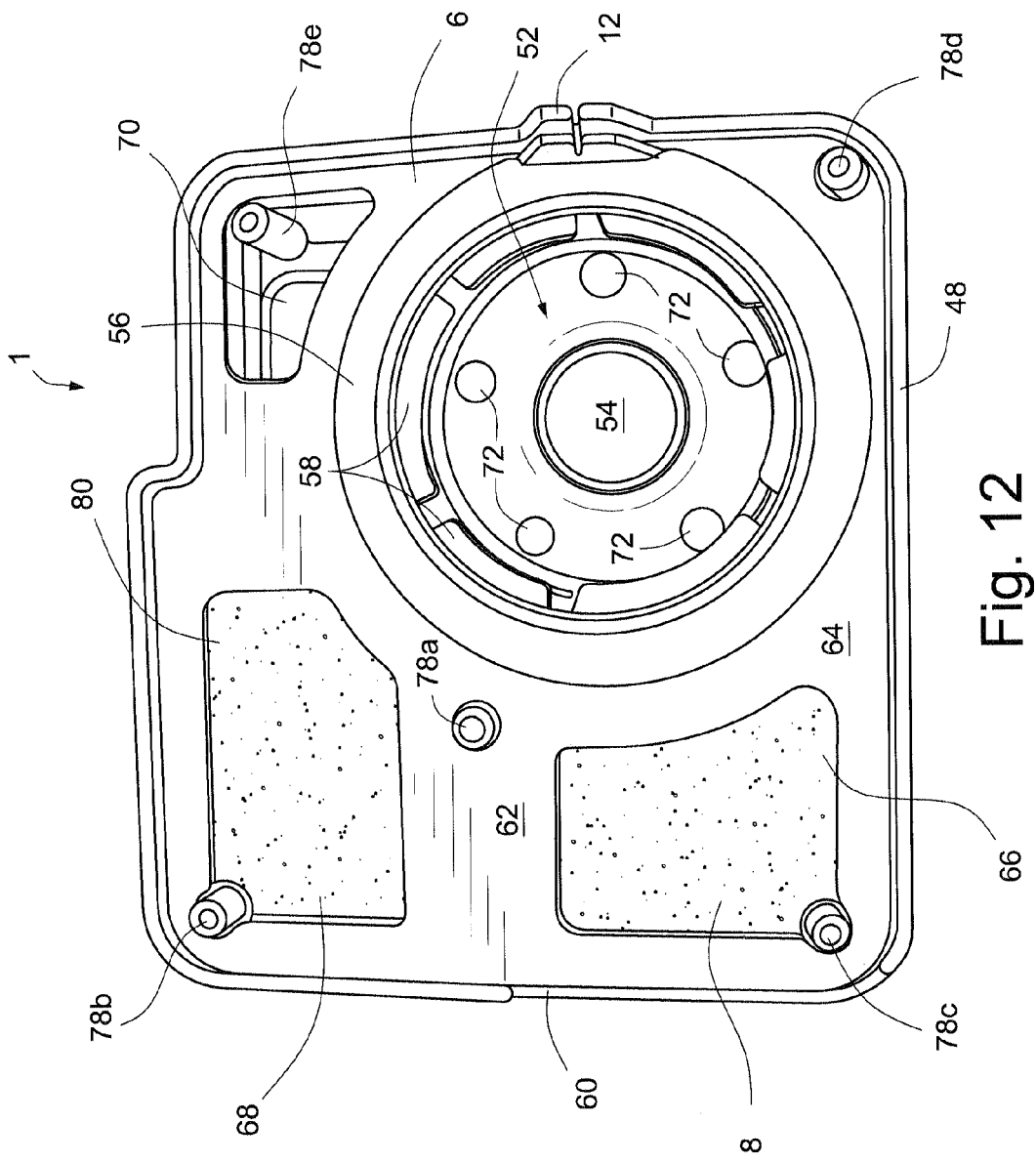
FIG. 12 is a perspective view of the lower chassis and flow generator seal after assembly.

Referring to FIG. 11, the flow generator seal 6 has a perimeter 82 that corresponds in shape to the perimeter of the lower chassis 4. As shown in FIG. 12, in the assembled condition, the flow generator seal 6 is provided around the lower chassis 4 so that the T-shaped skirt 48 of the flow generator seal 6 sealingly engages the perimeter of the lower chassis 4. The lower chassis fastener receptacles 78a-78d extend through the flow generator seal openings 50a-50d. The foam 8 is exposed through the air inlet seal opening 66 and the foam 80 is exposed through the blower inlet seal opening 68.

Blower and Blower Mount

Figure 13:
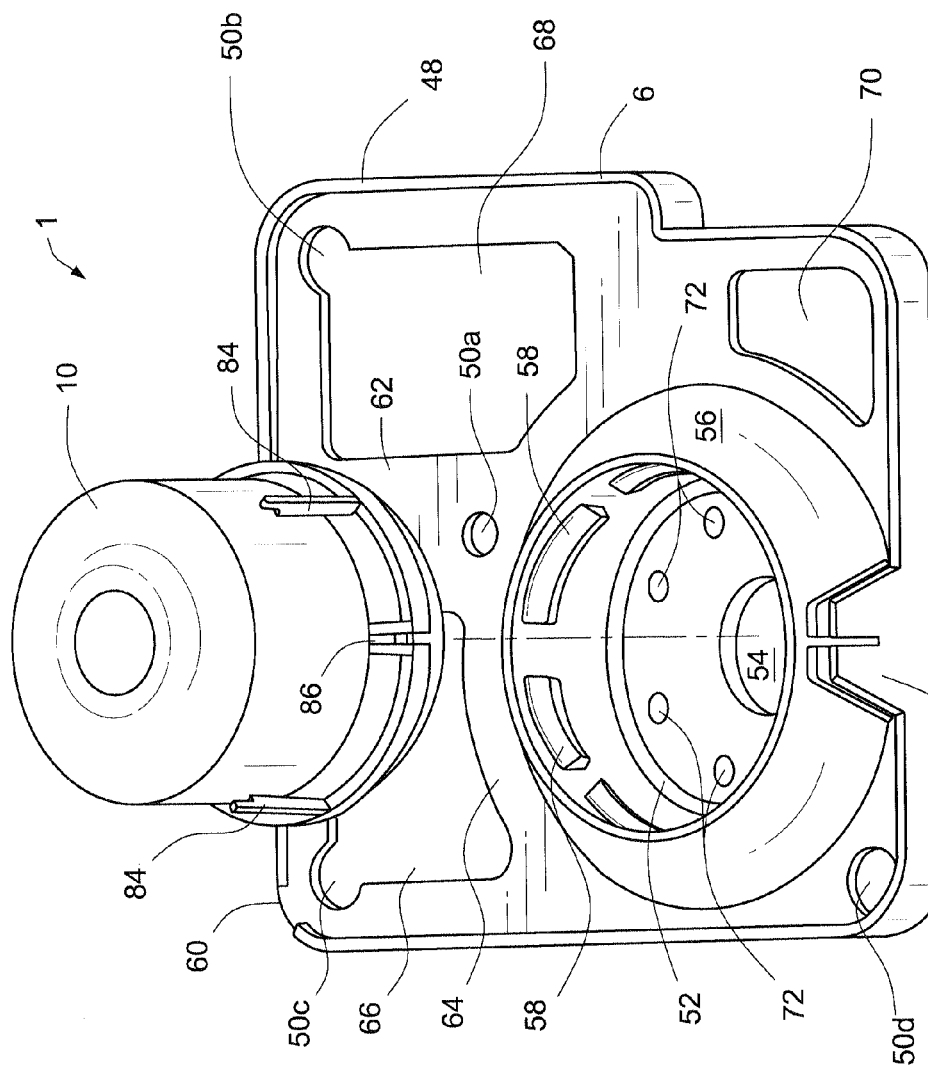
FIG. 13 is an exploded perspective view of the flow generator seal and a blower of the flow generator according to a sample embodiment.
Figure 14:
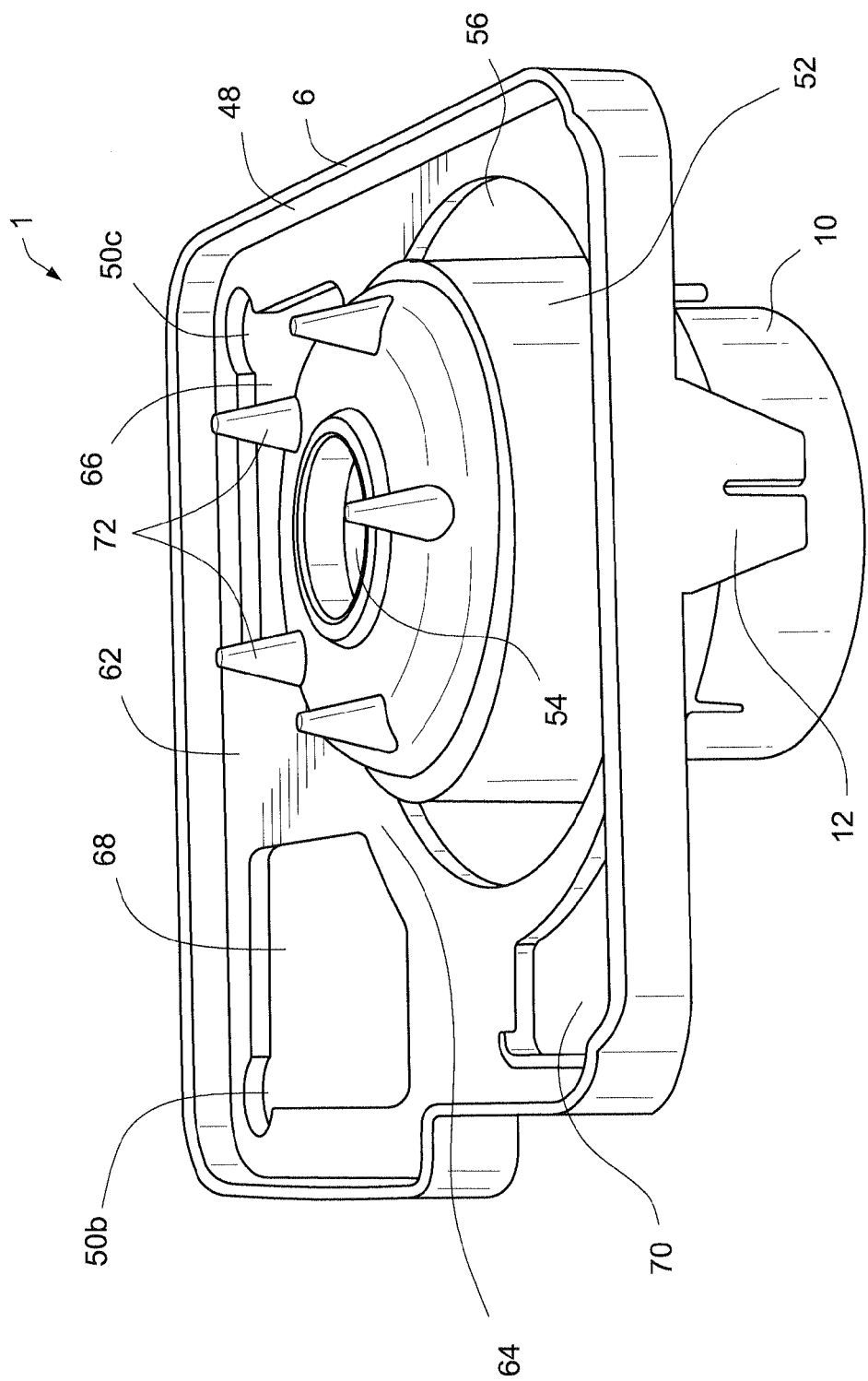
FIG. 14 is a perspective view of the blower and flow generator seal of FIG. 13 in an assembled condition.

Referring to FIGS. 13 and 14, the blower 10 is configured to be received in the blower receptacle mount 52 of the flow generator seal 6. The blower 10 may be as disclosed in, for example, in WO 2007/048205 A1, WO 2007/048206 A1, WO 2007/134405 A1, or U.S. Patent Application Publication 2008/0304986 A1, the entire contents of each being incorporated herein by reference. The motor and blower may be configured to provide a flow of breathable gas at a constant pressure, a variable pressure, or a bi-level pressure.

The outer periphery of the blower 10 may comprise blower alignment tabs 84 that are configured to be received between adjacent blower receptacle and mount ribs 58. The blower 10 also comprises a blower wire guide 86 that guides the wire from the motor of the blower 10 which is configured to be aligned with the wire grommet 12 of the flow generator seal 6, as shown in FIG. 15.

In use, when the blower 10 is running, the upper chassis 2 is the low pressure side and the lower chassis 4 is the high pressure side of the seal 6. The pressurized chamber causes the blower 10 to lift off the lower chassis 4 such that the blower 10 is suspended by the seal 6. The flow generator seal bump stops 72 and the upper chassis bump stops 38 are configured to prevent the blower 10 from bumping into the lower chassis 4 and the upper chassis 2, respectively.

Flow Generator Assembly

Figure 15:
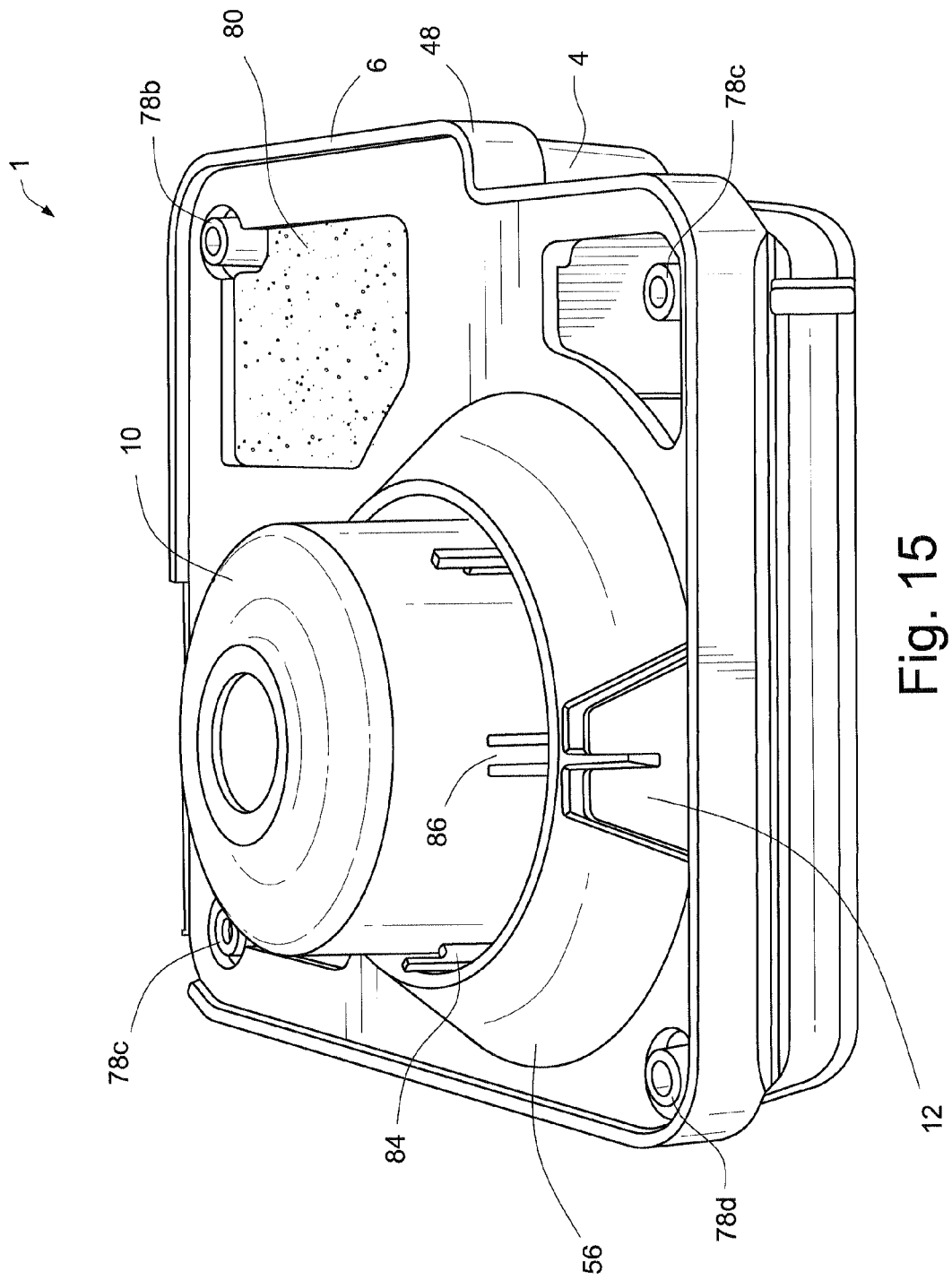
FIG. 15 is a perspective view of the flow generator seal and blower in an assembled condition.
Figure 16:
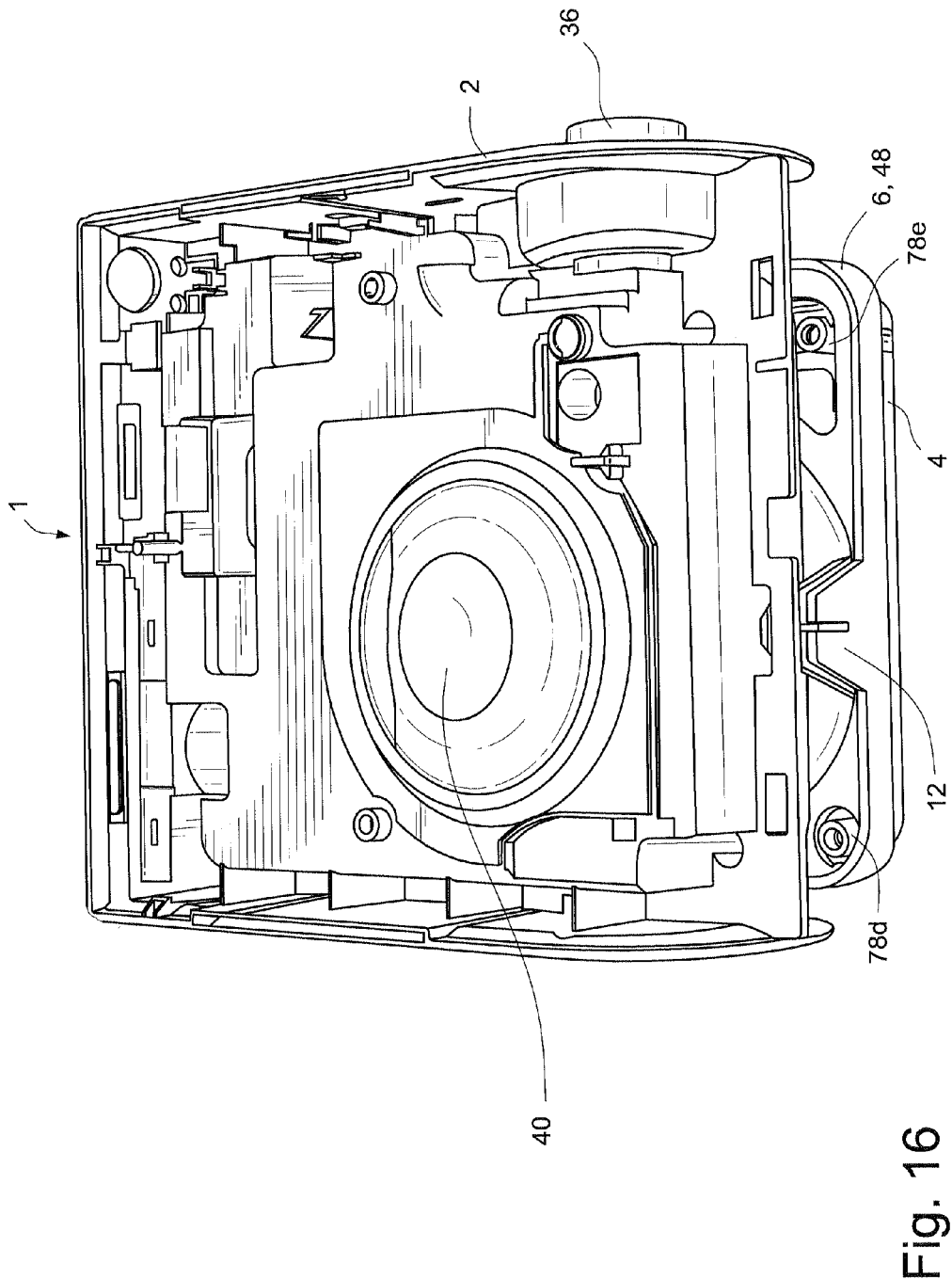
FIG. 16 is a perspective of the flow generator assembly prior to assembly according to one sample embodiment.

As shown in FIGS. 13-16, according to one sample embodiment of an assembly method, the flow generator seal 6 may be assembled with the blower 10, as shown in FIGS. 13 and 14. The flow generator seal and blower assembly 6, 10 may then be assembled on to the lower chassis 4 as shown in FIG. 15. Then, as shown in FIG. 16, the upper chassis 2 may be assembled to the lower chassis 4 and the flow generator seal and blower assembly 6, 10 shown in FIG. 15. The upper chassis 2 is assembled to the lower chassis 4 so that the blower 10 is received in the upper chassis receptacle top portion 40.

Figure 17:
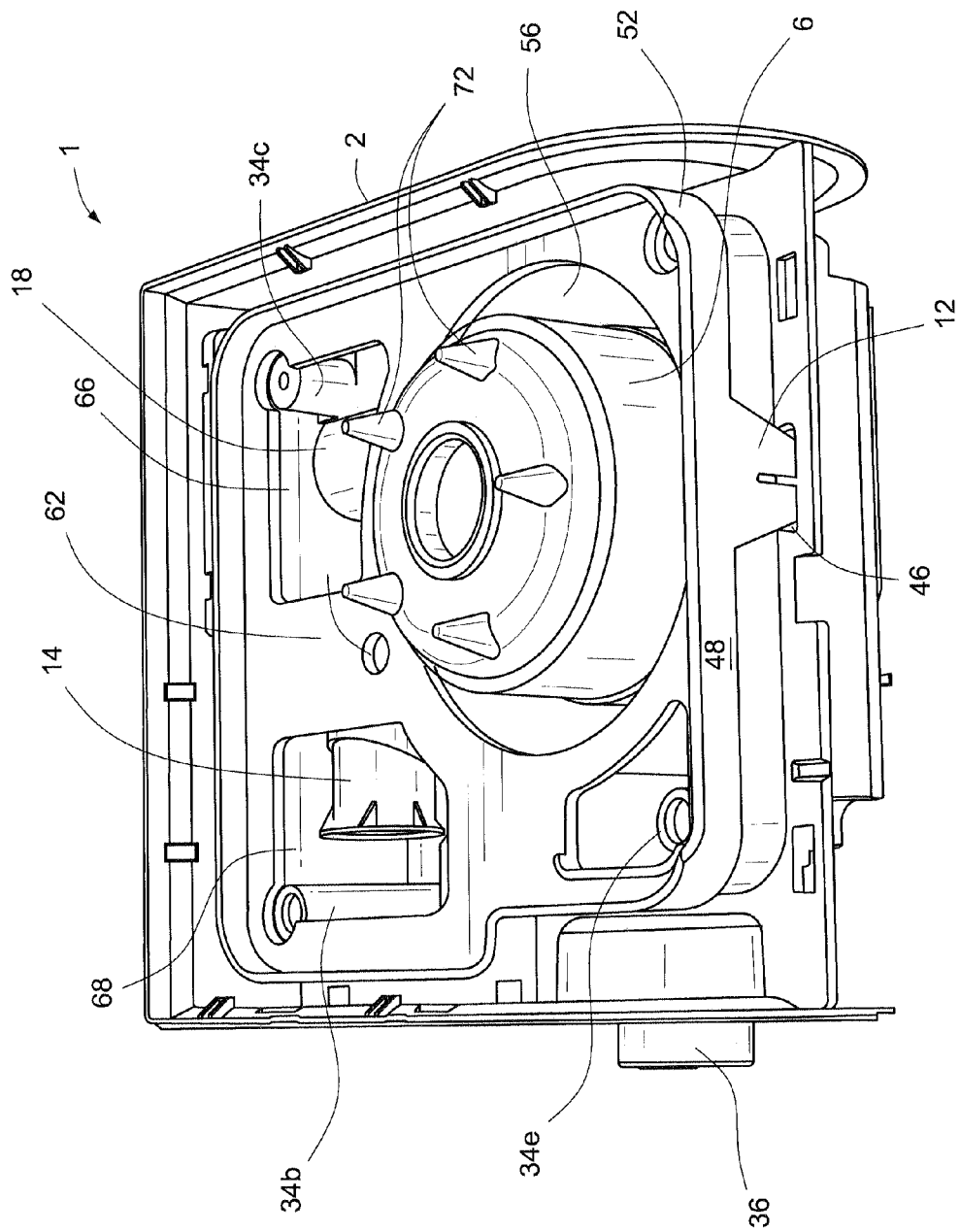
FIG. 17 is a perspective view of the flow generator seal and the upper chassis according to another sample embodiment of a method of assembly.
Figure 18:
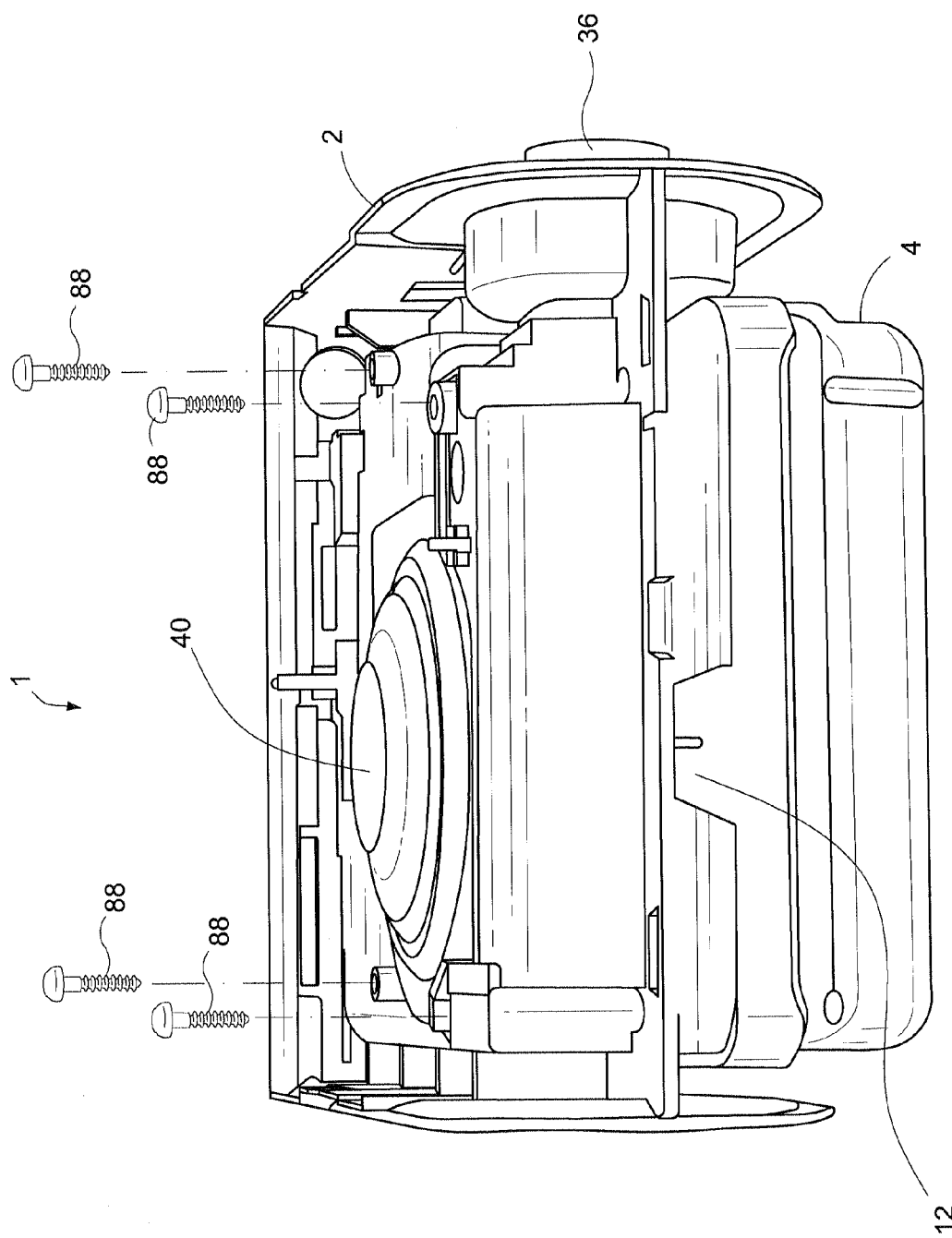
FIG. 18 is a perspective view of the flow generator prior to fastening of the upper chassis, flow generator seal, and lower chassis.

According to another sample embodiment of the assembly of the flow generator 1, the flow generator seal 6 may be assembled to the upper chassis 2 as shown in FIG. 17. The lower chassis 4 may then be assembled to the upper chassis 2 and the assembly fastened together by fasteners 88, as shown in FIG. 18.

According to another sample assembly embodiment, the upper chassis 2 is assembled with the flow tube 14. The blower 10 is then assembled with the flow generator seal 6. The wires of the motor of the blower 10 are routed through the blower wire guide 86 and the wire grommet 12 of the flow generator seal 6. The assembled flow generator seal and blower assembly 6, 10 is then aligned with the upper chassis 2 so that the wire grommet 12 aligns with the wire grommet notch 32 of the upper chassis 2. The assembled flow generator seal and blower assembly 6, 10 is then positioned on the upper chassis 2 and the flow generator seal 6 is stretched to make sure that the T-shaped skirt 48 is positioned outside the interior walls of the upper chassis 2.

The lower chassis 4 is then assembled with the foams 8, 80 and the lower chassis 4 is positioned on the flow generator seal 6. The T-shaped skirt 48 is then stretched around the perimeter 82 of the lower chassis 4 so that it fully surrounds the lower chassis 4. In an alternative embodiment, the seal may be sized to be a clearance fit over the perimeter 82 of the lower chassis 4, which may make assembly easier. The assembly is then fastened together by inserting the fasteners 88 in to the corresponding fastener receptacles 34a-34d, 78a-78d, respectively, of the upper chassis 2 and the lower chassis 4 and through the flow generator seal fastener openings 50a-50d. A fifth fastener may then be inserted into the fastener openings 34e, 78e of the upper chassis 2 and the lower chassis 4, respectively. The fifth fastener would pass through the air flow outlet seal opening 70 of the seal 6.

According to still another sample embodiment of the assembly method, the lower chassis 4 is assembled with the foams 8, 80. The blower 10 is then assembled with the flow generator seal 6 and positioned on the lower chassis 4. The T-shaped skirt 48 may be stretched so that the flow generator seal is sitting around the perimeter 82 of the lower chassis and the fastener openings 50a-50d of the flow generator seal 6 are provided around the fastener openings 78a-78d of the lower chassis 4. The wire of the motor of the blower 10 is routed through the blower wire guide 86 of the blower 10 and through the wire grommet 12 of the flow generator seal 6.

The upper chassis 2 is then assembled by securing the flow sensor 14 in to the upper chassis 2 with the flow sensor seal 16. The upper chassis 2 is then aligned with the lower chassis 4 so that the wire grommet 12 passes through the wire grommet slot 46 of the upper chassis 2 and is received in to the wire grommet notch 32 of the upper chassis 2. The assembly of the flow generator 1 is then completed by securing the fasteners 88 in to the fastener receptacles 34a-34d, 78a-78d, respectively, of the upper chassis 2 and the lower chassis 4 passing through the fastener openings 50a-50d in the flow generator seal 6. A fifth fastener may then be inserted into the fastener openings 34e, 78e of the upper chassis 2 and the lower chassis 4, respectively. The fifth fastener would pass through the air flow outlet seal opening 70 of the seal 6.

The seal mounts the motor and/or blower, provides alignment for the motor, and/or provides a suspension for the motor and/or blower. The seal also provides a seal between the high and low pressure sides of the motor and/or blower. The seal may seal the inlet air flow path and/or the outlet air flow path. The wire grommet seal seals the portion of the flow generator chassis assembly from which the wire of the motor extends. The seal also seals between acoustic chambers of the flow generator chassis assembly and/or seals the air flow path from the electronics of the flow generator. The seal may also include a flow sensor tube seal and manifold connection to the flow sensor. The provision of a seal capable of performing any or all of these functions reduces the part count and assembly time of the flow generator. The air flow path, not including the flow sensor, of the flow generator may be formed of three parts, i.e. the upper and lower chassis and the seal. The use of the upper and lower chassis along with the seal to form the air flow path allows the refinement of the upper and lower chassis, which may be formed for example of plastic, to achieve a high level of manufacturability at a lower cost.

While the technology has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A seal for a chassis assembly of a flow generator configured to provide a flow of breathable gas at a continuously positive pressure with respect to ambient air pressure to an entrance of a patient's airways including at least an entrance of a patient's nares, wherein the flow generator is configured to maintain a therapy pressure in a range of about 2 cm $H_2O$ to about 30 cm $H_2O$ above ambient air pressure throughout the patient's respiratory cycle, while the patient is sleeping, to ameliorate sleep disordered breathing, the chassis assembly including an upper chassis and a lower chassis, the seal comprising:

a blower receptacle sealing portion configured to seal a blower receptacle of the chassis assembly configured to receive a blower configured to generate the flow of breathable gas;

a flow sensor sealing portion configured to seal a flow sensor provided in the chassis assembly and configured to measure the flow of breathable gas;

a blower mount configured to receive a portion of the blower and mount the blower to the seal; and a blower mount suspension configured to suspend the blower mount from the blower receptacle sealing portion, wherein in an assembled condition the seal and the chassis assembly define a flow path from an inlet of the chassis assembly to the blower receptacle of the chassis assembly to an outlet of the chassis assembly.

2. A seal according to claim 1, further comprising:
an inlet sealing portion configured to seal the inlet of the chassis assembly.

3. A seal according to claim 1, further comprising:
an outlet sealing portion configured to seal the outlet of the chassis assembly.

4. A seal according to claim 1, further comprising:
a T-shaped skirt extending around a portion of the seal and configured to seal a junction between the upper chassis and the lower chassis.

5. A seal according to claim 4, wherein the T-shaped skirt does not extend around the seal in a region of the inlet of the chassis assembly, and the seal comprises an L-shaped skirt in the region of the inlet of the chassis assembly.

6. A seal according to claim 1, further comprising:
a plurality of openings configured to receive a respective plurality of fasteners configured to fasten the upper chassis and the lower chassis together.

7. A seal according to claim 1, further comprising:
a grommet configured to receive a wire of the blower.

8. A seal according to claim 7, wherein the blower mount comprises a means for aligning the blower so the wire of the blower is received in the grommet.

9. A seal according to claim 7, wherein the blower mount comprises a plurality of projections configured to engage a plurality of alignment tabs of the blower to align the blower.

10. A seal according to claim 1, wherein the blower mount comprises at least one bump stop configured to engage the chassis assembly to prevent the blower from engaging the chassis assembly.

11. A seal according to claim 1, wherein the blower mount comprises an outlet corresponding to an outlet of the blower.

12. A seal according to claim 1, wherein the blower mount suspension comprises a frusto-conical portion between the blower mount and the blower receptacle sealing portion.

13. A seal according to claim 2, further comprising:
an inlet seal opening in a region adjacent the inlet sealing portion.

14. A seal according to claim 1, further comprising:
a blower inlet seal opening in a region adjacent the blower receptacle sealing portion.

15. A seal according to claim 3, further comprising:
an outlet seal opening in a region adjacent the outlet sealing portion.

16. A seal according to claim 1, wherein a perimeter of the seal corresponds to a perimeter of the lower chassis and/or the perimeter of the upper chassis.

17. A seal according to claim 1, wherein the seal is formed of a flexible material.

18. A seal according to claim 1, wherein the seal is formed of an elastically deformable material.

19. A seal according to claim 1, wherein the seal is formed of silicone.

20. A seal according to claim 19, wherein the seal is transparent or translucent.

21. A seal according to claim 1, further comprising a frame or support.

22. A seal according to claim 21, wherein the frame or support comprises a rigid skeleton.

23. A seal according to claim 21, wherein the frame or support is overmolded onto the seal.

24. A flow generator for generating a flow of breathable gas, the flow generator comprising:
a chassis assembly comprising a lower chassis and an upper chassis, the lower chassis and the upper chassis defining a blower receptacle;
a blower provided in the blower receptacle; and
a seal according to claim 1.

25. A flow generator according to claim 24, wherein the upper chassis comprises an inlet and an outlet.

26. A flow generator according to claim 24, wherein the upper chassis comprises a blower receptacle top portion, and the blower receptacle top portion comprises at least one bump stop configured to engage the blower to prevent the blower from engaging the blower receptacle top portion.

27. A flow generator according to claim 24, further comprising a flow sensor configured to measure the flow of breathable gas.

28. A flow generator according to claim 27, wherein the flow sensor is provided between two walls of the upper chassis, and further comprising a flow sensor seal configured to mount the flow sensor between the two walls and a flow sensor seal around a periphery of the flow sensor.

29. A flow generator according to claim 28, further comprising a pressure sensor and/or a thermistor and a pressure sensor seal and/or a thermistor seal.

30. A flow generator according to claim 28, wherein the seal and the flow sensor seal and/or the pressure sensor seal and/or the thermistor seal are integrally formed.

31. A flow generator according to claim 24, wherein the upper chassis comprises a notch to receive a first portion of a grommet of the seal, the grommet being configured to receive a wire of the blower.

32. A flow generator according to claim 31, wherein the upper chassis comprises a slot to receive a second portion of the grommet of the seal.

33. A flow generator according to claim 24, wherein the upper chassis and the lower chassis comprise a plurality of corresponding fastener receptacles configured to receive a plurality of fasteners to secure the upper chassis and lower chassis in an assembled condition.

34. A flow generator according to claim 24, further comprising:
foam provided in the lower chassis in a region adjacent the inlet sealing portion of the seal and corresponding to the inlet seal opening of the seal.

35. A flow generator according to claim 24, further comprising:
foam provided in the lower chassis in a region adjacent the blower inlet sealing portion of the seal and corresponding to the blower inlet seal opening.

36. A flow generator according to claim 25, further comprising:
a filter provided in the inlet of the upper chassis.

37. A flow generator according to claim 24, wherein the blower comprises a wire guide configured to guide a wire of a motor of the blower to a grommet of the seal.

38. A seal according to claim 1, wherein the blower mount comprises a recess.

39. A seal according to claim 38, wherein the seal and the chassis assembly together define the flow path from the inlet of the chassis assembly to the blower receptacle of the chassis assembly and together define the flow path from the blower receptacle of the chassis assembly to outlet of the chassis assembly.

40. A seal according to claim 1, wherein the flow sensor sealing portion is configured to contact the flow sensor.

41. A flow generator for generating a pressurized flow of breathable gas at a continuously positive pressure with respect to ambient air pressure to an entrance of a patient's airways including at least an entrance of a patient's nares, wherein the flow generator is configured to maintain a therapy pressure in a range of about 2 cm H$_2$O to about 30 cm H$_2$O above ambient air pressure throughout the patient's respiratory cycle, while the patient is sleeping, to ameliorate sleep disordered breathing, comprising:
   a chassis comprising a lower chassis and an upper chassis, the lower chassis and the upper chassis defining an enclosure;
   a blower provided in the enclosure and configured to generate the flow of breathable gas from air drawn through an inlet in the chassis and deliver the flow of breathable gas to an outlet in the chassis; and
   a blower mount between the lower chassis and the upper chassis that mounts the blower in the enclosure, the blower mount comprising:
      a blower receptacle that receives a lower portion of the blower,
      a blower mount outlet configured to deliver the flow of breathable gas from the blower to the outlet in the chassis, and
      a seal in engagement with the upper chassis and configured to provide a substantially sealed air flow path upstream of the blower receptacle and a substantially sealed air flow path from an inlet of an upper chassis blower receptacle to the blower mount outlet.

42. A flow generator according to claim 41, wherein the seal extends substantially around the blower receptacle.

43. A flow generator according to claim 42, wherein the seal comprises an air flow outlet seal opening through which the flow of breathable gas passes from the blower mount outlet to the outlet of the chassis.

44. A flow generator according to claim 43, wherein the blower mount comprises at least one aperture through which at least one fastener passes.

45. A flow generator according to claim 44, wherein the upper chassis comprises at least one aperture corresponding to the at least one aperture of the blower mount, and the at least one fastener passes through the at least one aperture of the upper chassis and the at least one aperture of the blower mount.

46. A flow generator according to claim 45, further comprising a grommet that holds at least one electrical wire extending from the blower.

47. A flow generator according to claim 46, wherein the upper chassis comprises a grommet slot through which the grommet passes.

48. A flow generator according to claim 47, wherein the inlet of the upper chassis blower receptacle is provided in a side wall of the upper chassis blower receptacle.

49. A flow generator according to claim 48, wherein the upper chassis blower receptacle comprises a top portion that receives a top portion of the blower.

50. A flow generator according to claim 49, wherein the upper chassis blower receptacle top portion comprises at least one upper chassis stop configured to prevent the blower from contacting the upper chassis.

51. A flow generator according to claim 50, wherein the blower mount comprises at least one stop configured to prevent the blower from contacting the lower chassis.

52. A flow generator according to claim 51, wherein the blower comprises a motor having an axis that is perpendicular to an axis of the outlet of the chassis.

53. A flow generator according to claim 52, wherein the axis of the motor is perpendicular to an axis of the inlet of the chassis.

54. A flow generator according to claim 53, wherein the axis of the outlet of the chassis is perpendicular to the axis of the inlet of the chassis.

55. A flow generator according to claim 54, further comprising a flow sensor.

56. A flow generator according to claim 55, further comprising a filter provided at the inlet of the chassis.

57. A flow generator according to claim 56, further comprising a foam material between the blower mount and the lower chassis.

58. A flow generator according to claim 57, wherein the blower mount comprises at least one flange that engages the lower chassis to secure the blower mount to the lower chassis.

59. A flow generator according to claim 58, wherein the blower mount is transparent or translucent.

60. A flow generator according to claim 59, wherein the blower mount comprises an inlet opening that receives an air flow from the inlet of the chassis.

61. A flow generator according to claim 60, wherein the blower mount and the upper chassis define an air flow path from the blower mount inlet opening to the inlet of the upper chassis blower receptacle.

62. A flow generator according to claim 41, wherein the upper chassis blower receptacle is a subassembly in the upper chassis and is configured to receive an upper portion of the blower.

63. A flow generator according to claim 62, wherein the blower receptacle comprises a recess.

64. A flow generator for generating a pressurized flow of breathable gas at a continuously positive pressure with respect to ambient air pressure to an entrance of a patient's airways including at least an entrance of a patient's nares, wherein the flow generator is configured to maintain a therapy pressure in a range of about 2 cm H$_2$O to about 30 cm H$_2$O above ambient air pressure throughout the patient's respiratory cycle, while the patient is sleeping, to ameliorate sleep disordered breathing, comprising:
   a chassis defining a chassis blower receptacle;
   a blower provided in the chassis blower receptacle and configured to generate the flow of breathable gas from air drawn through an inlet in the chassis and deliver the flow of breathable gas to an outlet in the chassis; and
   a blower mount that mounts the blower in the chassis blower receptacle, the blower mount comprising:
      a blower receptacle that receives a lower portion of the blower,
      a blower mount outlet configured to deliver the flow of breathable gas from the blower to the outlet in the chassis, and
      a seal in engagement with the chassis configured to provide a substantially sealed air flow path upstream of the blower mount blower receptacle and a substantially sealed air flow path from an inlet of the chassis blower receptacle to the blower mount outlet.

65. A flow generator according to claim 64, wherein the chassis blower receptacle comprises a subassembly within the chassis that receives an upper portion of the blower.

66. A flow generator according to claim 65, wherein the blower receptacle comprises a recess.

67. A flow generator according to claim 66, wherein the chassis comprises an air inlet and an air outlet and the blower mount provides a substantially sealed air flow path from the chassis air inlet to the chassis air outlet.

68. A flow generator according to claim 67, wherein the blower mount comprises an inlet sealing portion that seals the inlet of the chassis and an outlet sealing portion configured to seal the outlet of the chassis.

69. A flow generator according to claim 68, wherein the blower mount comprises a grommet that receives a wire from the blower.

70. A flow generator according to claim 69, further comprising a flow sensor configured to measure the flow of breathable gas.

71. A flow generator according to claim 70, wherein the blower mount further comprises a sensor seal portion that mounts the flow sensor between two walls of the chassis and form a seal around a periphery of the flow sensor.

* * * * *